(12) United States Patent
Sher

(10) Patent No.: US 7,734,332 B2
(45) Date of Patent: Jun. 8, 2010

(54) ATHERECTOMY SYSTEM WITH IMAGING GUIDEWIRE

(75) Inventor: Arieh Sher, Rehovot (IL)

(73) Assignee: Ariomedica Ltd., Tel Aviv (IL)

( * ) Notice: Subject to any disclaimer, the term of this patent is extended or adjusted under 35 U.S.C. 154(b) by 530 days.

(21) Appl. No.: 10/531,184

(22) PCT Filed: Oct. 8, 2003

(86) PCT No.: PCT/IL03/00807
§ 371 (c)(1), (2), (4) Date: Apr. 11, 2005

(87) PCT Pub. No.: WO2004/034869
PCT Pub. Date: Apr. 29, 2004

(65) Prior Publication Data
US 2006/0015126 A1    Jan. 19, 2006

Related U.S. Application Data

(60) Provisional application No. 60/419,087, filed on Oct. 18, 2002.

(51) Int. Cl.
*A61M 25/00* (2006.01)
(52) U.S. Cl. ........................ 600/434; 606/159; 600/585; 600/433; 600/425
(58) Field of Classification Search ......... 606/191–198, 606/159, 108; 600/407, 425, 479, 585, 433, 600/434
See application file for complete search history.

(56) References Cited

U.S. PATENT DOCUMENTS

| 4,728,319 | A | * | 3/1988 | Masch ........................ 604/22 |
| 4,794,931 | A | | 1/1989 | Yock |
| 5,047,040 | A | * | 9/1991 | Simpson et al. ............. 606/159 |
| 5,100,424 | A | * | 3/1992 | Jang et al. .................... 606/159 |
| 5,318,576 | A | * | 6/1994 | Plassche et al. ............. 606/159 |
| 5,350,390 | A | | 9/1994 | Sher |
| 5,409,454 | A | | 4/1995 | Fischell |
| 5,429,136 | A | * | 7/1995 | Milo et al. ................... 600/439 |
| 5,569,276 | A | * | 10/1996 | Jang et al. .................... 606/159 |
| 5,582,171 | A | * | 12/1996 | Chornenky et al. ......... 600/425 |
| 5,697,459 | A | | 12/1997 | Sher |
| 5,806,404 | A | | 9/1998 | Sher |
| 5,938,609 | A | | 8/1999 | Pomeranz |
| 5,993,469 | A | * | 11/1999 | McKenzie et al. .......... 606/159 |
| 5,997,557 | A | * | 12/1999 | Barbut et al. ................ 606/159 |
| 6,120,516 | A | * | 9/2000 | Selmon et al. .............. 606/159 |
| 6,228,076 | B1 | | 5/2001 | Winston |
| 6,377,048 | B1 | | 4/2002 | Golan |
| 6,398,798 | B2 | * | 6/2002 | Selmon et al. .............. 606/159 |
| 6,445,939 | B1 | | 9/2002 | Swanson |
| 6,459,921 | B1 | | 10/2002 | Belef |

(Continued)

*Primary Examiner*—Brian Casler
*Assistant Examiner*—Joel M Lamprecht
(74) *Attorney, Agent, or Firm*—Mark M. Friedman

(57) ABSTRACT

Systems and methods of increasing blood flow in a blood vessel with ultraluminal plaque. One disclosed method includes inserting an imaging guidewire into the blood vessel to the intraluminal plaque, propelling a catheter with a working head over the guidewire towards the distal end of the guidewire, scanning with the imaging guidewire to generate a cross-section image, radially positioning the catheter using a positioning element, monitoring the image to ascertain that the working head is properly positioned and operating the working head to remove the plaque. A computerized system designed, constructed and configured to perform the methods is further disclosed.

36 Claims, 7 Drawing Sheets

U.S. PATENT DOCUMENTS

| | | | |
|---|---|---|---|
| 6,623,495 B2 * | 9/2003 | Findlay et al. | 606/159 |
| 6,852,097 B1 * | 2/2005 | Fulton, III | 604/266 |
| 2001/0018596 A1 * | 8/2001 | Selmon et al. | 606/198 |
| 2002/0019644 A1 * | 2/2002 | Hastings et al. | 606/159 |
| 2002/0077642 A1 * | 6/2002 | Patel et al. | 606/167 |
| 2005/0113853 A1 * | 5/2005 | Noriega et al. | 606/159 |

* cited by examiner

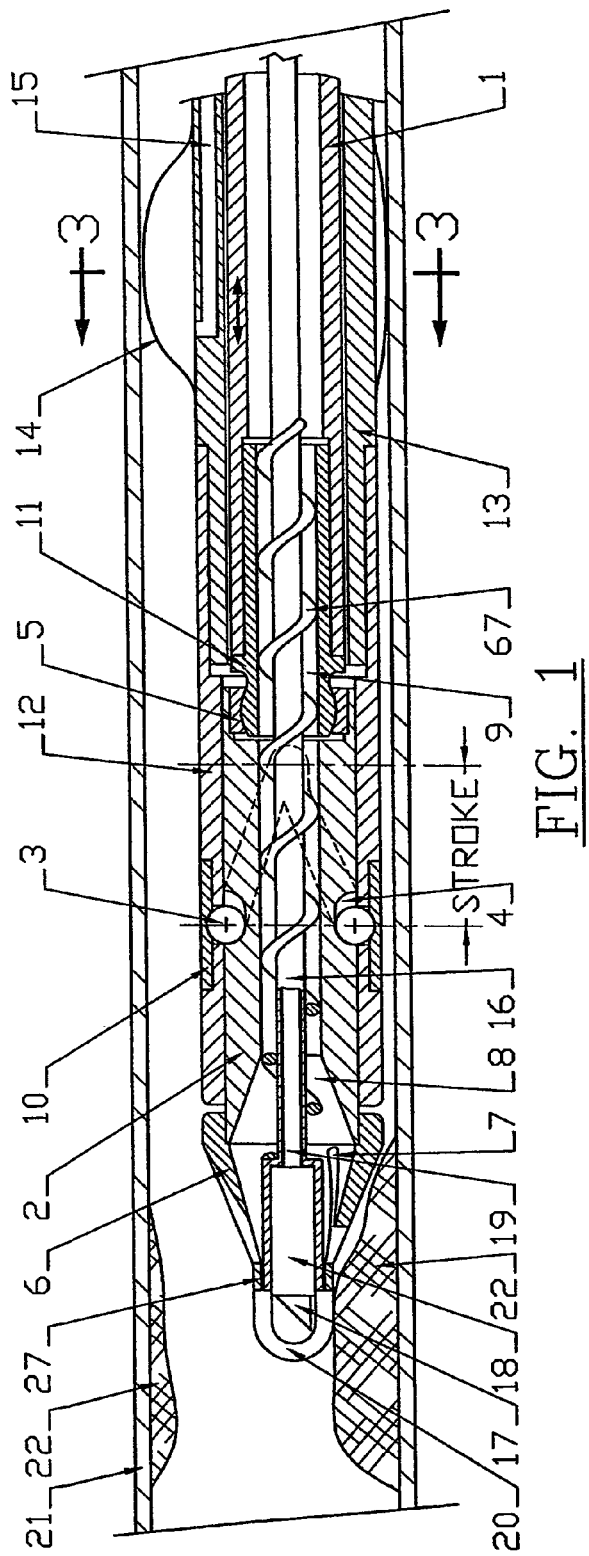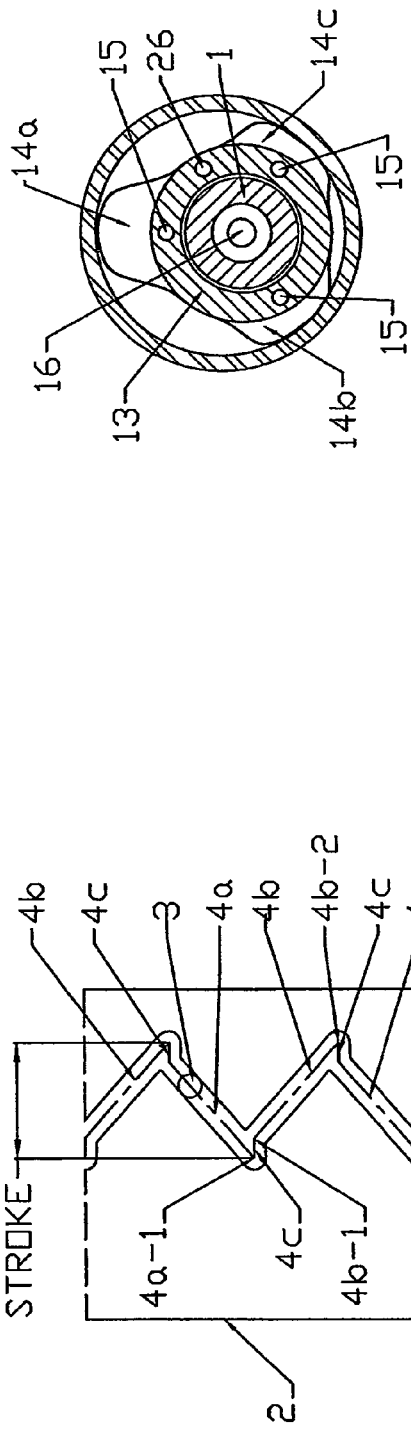
FIG. 1
FIG. 2
FIG. 3

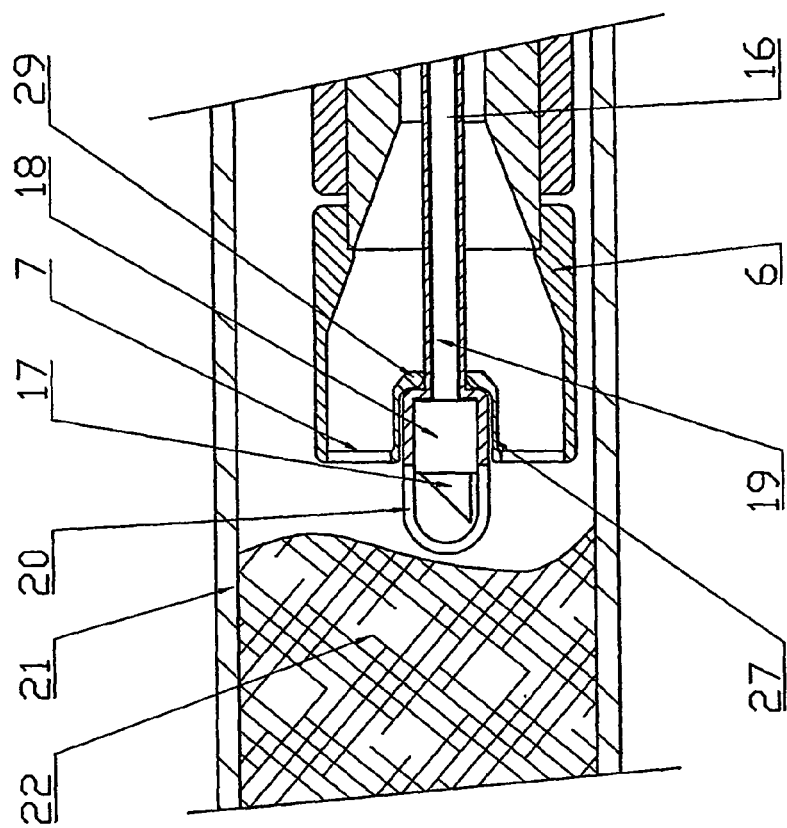
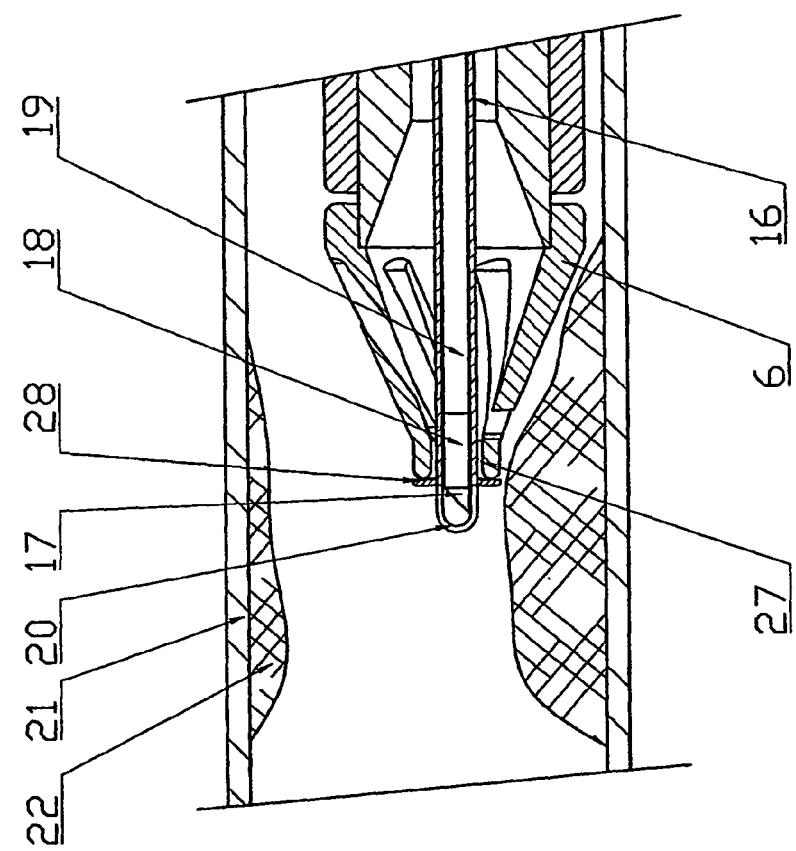

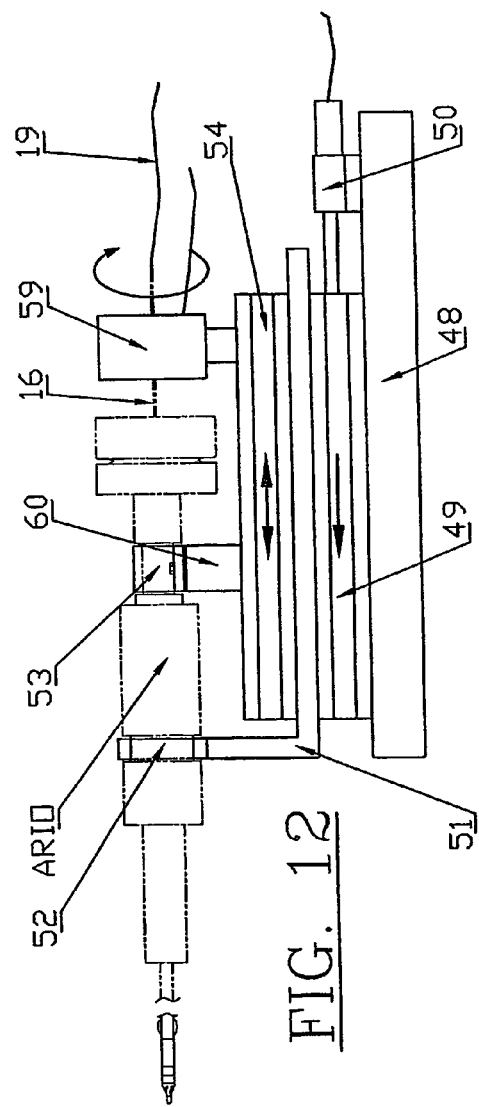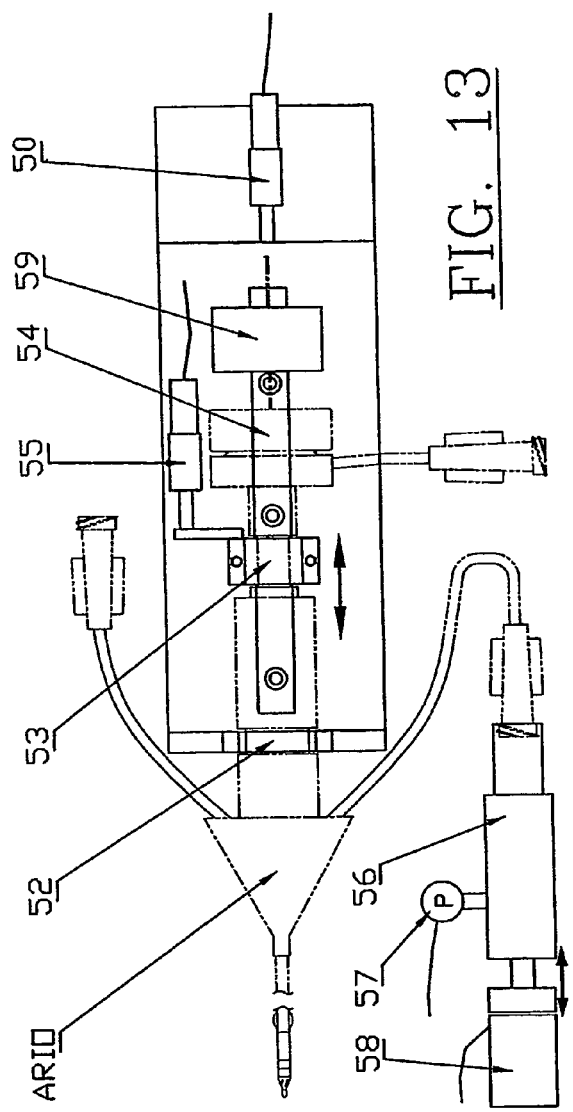
FIG. 12
FIG. 13

ATHERECTOMY SYSTEM WITH IMAGING GUIDEWIRE

This application claims priority from U.S. Patent Application 60/419,087 filed on Oct. 18, 2002.

FIELD AND BACKGROUND OF THE INVENTION

The present invention is directed to minimally invasive surgical systems and methods of use thereof. More specifically, the present invention is directed to computerized systems for operation of atherectomy instruments and methods for intravascular surgery to increase blood flow in a lumen of a blood vessel. The disclosures of U.S. Pat. Nos. 5,350,390, 5,806,404 and 5,697,459, issued to Sher, are incorporated herein by reference in their entirety.

Atherosclerosis is the principal cause of heart attacks, stroke, gangrene and loss of function of extremities. It accounts for approximately 50% of all mortalities in the USA, Europe and Japan. Atherosclerosis is characterized by a build-up of fatty deposits in the intimal layer of a patient's blood vessels. Very often over time, what is initially deposited as relatively soft cholesterol-rich atheromatous material hardens into a calcified atherosclerotic plaque. Such atheromas restrict the flow of blood, which results in chest pain or even in cases severe restriction, to heart attack. Restriction of blood flow, which leads to heart attack, is also explained by another mechanism known as vulnerable plaque. It happens to people that do not have severely narrowed arteries. In fact the vulnerable plaque may be buried inside the artery wall and may not always bulge out and block the blood flow through the artery. Inflammation combined with other stress e.g., high blood pressure can cause the covering over the plaque to crack and bleed, spilling the contents of the vulnerable plaque into the blood stream. Blood cells that recruit to the site of injury can form a clot large enough to block the artery. It is of enormous importance that the physician will have the capability of imaging the lesion morphologically as well as the plaque composition. There are imaging techniques that perform these tasks. The modalities of imaging techniques will be detailed later.

The present therapeutic strategies for severe atherosclerosis in coronary arteries rely on angioplasty procedures (e.g., percutaneous trans-luminal coronary angioplasty (PTCA), atherectomy devices, stent implantation, excimer laser angioplasty, etc.), and coronary artery bypass surgery (CABG). Transluminal angioplasty refers to a technique of dilating significantly blocked arteries from inside, thus avoiding the need for much more extensive surgical intervention (CABG).

Conceptually, atherectomy devices have the advantage of positively removing the plaque. In the balloon (PTCA) and the stent procedures the plaque is not removed but rather pushed towards the blood vessel wall. Several kinds of atherectomy devices are currently available but their performances have not stood up to the expectations and will be discussed later. A major disadvantage of the stent is that it causes in-stent restenosis, a phenomenon that will be explained later. Stent implantation involves deployment of a foreign body that evokes a reaction of the immune system. The stent and the balloon have the advantage that the procedure is relatively simple and easy to use.

Today the stent is the common procedure for clearing blocked arteries (97% of more than 2 million procedures world wide). Atherectomy devices are used only for specific procedures such as debulking of calcified lesions where it is difficult to open the lesion with the balloon.

To date none of the available techniques provides a total safe and effective solution to blocked arteries. The problems that still exist in clearing blocked arteries are described below:

Restenosis—

Restenosis is re-occlusion of a peripheral or coronary artery following trauma to the artery caused by efforts to clear an occluded portion of the artery by angioplasty, such as, balloon dilation, stent implantation, atherectomy or laser ablation treatment. The rate of restenosis following treatment with these angioplasty procedures is about 30-50% depending upon the vessel location, lesion length and a number of other variables. Restenosis occurs also in grafts that are used to bypass blocked arteries. Restenosis results in significant morbidity and mortality and frequently necessitates further interventions, such as repeat angioplasty or coronary bypass surgery. Thus, there is a need for methods and devices for preventing and/or treating restenosis. Preferably, these methods and devices should be specific in their effect, easy to administer, and effective in the long run with minimal adverse side effects. The processes responsible for restenosis are not completely understood.

One aspect of restenosis may be simply mechanical, caused by the elastic rebound of the arterial wall. Another aspect of restenosis is believed to be a natural healing reaction to the injured arterial walls that were damaged by angioplasty procedures. The final result of the complex steps of the healing process which involve local inflammation is intimal hyperplasia, and migration and proliferation of medial smooth muscle cells, until the artery is again occluded.

The existing, FDA approved, atherectomy devices have shown a high rate of restenosis (30-50%). Atherectomy devices have also additional technical problems. The Athero-Cath (Guidant) is complex to use, is pushed across the lesion and offers inconsistent results. It has a high rate of blood vessel perforation. The Rotablator (Boston Scientific) is applicable only to moderate to heavily calcified atherosclerotic plaque lesions. It does not cut the plaque but rather pulverizes it while rotating at a very high speed. This causes problem of heating the blood vessel and also to the phenomenon known as No Reflow in which blood does not flow in the vessel even though the lesion was opened.

In another type of atherectomy device, the cutting head does not rotate. An example of this type of device is U.S. Pat. No. 5,409,454 to Fischell. In this type of device, the cutting head is first pushed across the lesion and then pulled back. While pulled back the cutting head shaves the atheroma. Pushing the catheter across the lesion causes trauma to the blood vessel.

My U.S. Pat. No. 5,350,390 describes an atherectomy device, that addresses the trauma problem. However, my own earlier teachings do not include the idea that removal of a lesion may begin prior to transversal of the lesion by a guidewire. This serious inherent disadvantage is addressed by the teachings of the present invention, as will be detailed hereinbelow. In order to differentiate the claimed invention from those earlier teachings, the invention will be referred to hereinbelow as Apparatus for Removal of Intraluminal Occlusions (ARIO)

In-Stent Restenosis—

The mechanical aspects of restenosis have been successfully addressed by the use of stents to prevent elastic rebound of the vessel, thereby reducing the level of restenosis for many patients. The stent, though, has created a new problem called in-stent restenosis, namely the occurrence of excessive late intimal hyperplasia due to excessive cell proliferation that can restrict blood flow within the stent itself. In-stent restenosis occurs in 20-30% of stent procedures and in many cases CABG is required to solve the problem.

Brachytherapy and drug coated stents are approaches aimed to reduce in-stent restenosis. Brachyterapy provides only partial solution to in-stent restenosis. The drug coated stents succeeded in reducing in-stent restenosis from 20-30% to 5-9% but failed to eliminate it. The drug-coated stent is a new procedure. In follow-up tests, problems such as late incomplete apposition emerged, however no long-term results are currently available.

Existing atherectomy devices such as the Rotablator and AtheroCath were tested for clearing in-stent restenosis, but the results were disappointing. ARIO, due to its mild mode of operation is a suitable candidate for clearing in-stent restenosis.

Perforation—Coronary artery perforation is a rare but important complication of percutaneous revascularization. Perforation has been reported in lesions treated with PTCA and Stents and at much higher rate in atherectomy devices. During PTCA or stenting perforation may occur as a consequence of guidewire advancement, balloon inflation or balloon rupture. Regardless of the device, the risk of perforation is increased when complex lesion is present (chronic total occlusion, vessel bifurcation, severe tortuosity in artery). Clinically, coronary perforation is associated with a high incidence of death.

Total Occlusions (TO) is a formidable obstacle for physicians. Physicians cannot see the path for the guidewire through the TO because the flow of the angiography contrast media is stopped by the blockage. There is a higher risk of perforation or damaging the vessel than with normal angioplasty. U.S. Pat. No. 6,228,076 to Winston is an example of controlling the path of the guidewire across a lesion using OCT. Another example for TO crossing is U.S. Pat. No. 6,120,516 to Selmon.

Bifurcation: Percutaneous coronary intervention (PCI) in bifurcation lesions is challenging. It has lower procedural success and high rates of restenosis compared with non-bifurcation PCI.

A great part of the problems described above can be solved if the physician is provided with means for imaging the arteries. An important and standard imaging modality is angiography. However, angiography enables the physician to see only a general view of the arteries, where the details of the plaque are not clear. Several modalities that can give a detailed image of the plaque have been suggested. These modalities allow the physician to visualize the morphology as well as the composition of the plaque. Subsequently, the physician can position the working head of the intraluminal catheter at a desired location. This procedure could minimize remarkably the risk of blood vessel perforation.

The imaging modalities can be classified in the following hierarchical manner:

There are two types of blood vessel imaging techniques, non-invasive and minimally invasive. The non-invasive modalities include CT (X-ray Computer Tomography), MRI (Magnetic Resonance Imaging), ECBT (Electron Beam Computer Tomography), etc. In current non-invasive technology the resolution of the image is poor and therefore this type of imaging can be used for a general view of the arteries. The minimally invasive imaging can be divided into two classes: The first incorporates an imaging sensor into or on the catheter. This class is exemplified by U.S. Pat. No. 4,794,931 to Yock, which describes an atherectomy device with ultrasonic imaging capabilities.

The second class incorporates a sensor into a guidewire. The second class can be divided into two sub-classes. The first sub-class produces a cross sectional image of the lumen e.g., IVUS (Intravascular Ultrasound)—U.S. Pat. No. 6,459,921 to Belef, OCT (Optical Coherence Tomography)—U.S. Pat. No. 6,445,939 to Swanson, MRI (Magnetic Resonance Imaging)—U.S. Pat. No. 6,377,048 to Golan. This sub-class is relevant to the present invention, as the operation of the device is based on the fact that the physician can see a cross sectional view of the lumen.

The second sub-class does not provide a cross sectional image of the lumen. It provides other kind of information related to the lumen e.g., Thermography supplies thermal mapping of the interior of the lumen, U.S. Pat. No. 6,228,076 to Winston, describes a system which receives interferometric data from the tissue, etc.

Prior art describes a device that incorporates an imaging guidewire that can produce a cross sectional view of the lumen into an intravascular catheter. U.S. Pat. No. 5,938,609 to Pomeranz describes an imaging guidewire with an ultrasound sensor. The movable imaging guidewire includes a fixed guidewire tip attached to its distal end. The movable imaging guidewire is first positioned within the vascular system so that its fixed guidewire tip extends beyond the stenosed region, and than the intravascular catheter is inserted over the movable imaging guidewire. This mode of operation renders it suitable for balloons procedures. The disadvantages of this type of movable imaging guidewire are similar to the standard guidewire, i.e., the mechanical requirements of pushability and crossability are high. The operational disadvantage is high risk of perforating the blood vessel or in case the occlusion is too severe the guidewire cannot cross it.

SUMMARY OF THE INVENTION

The present invention is directed to improvements of ARIO. The unique features of ARIO allow clearing of blocked arteries, removing vulnerable plaque, clearing in-stent restenosis, opening totally occluded arteries and removing plaque at bifurcation.

It is the object of the present invention to provide a minimally invasive device for removing intraluminal occlusions in a safe, gentle and controlled manner.

It is the object of the present invention to provide a minimally invasive device that is guided by a non-crossing the lesion imaging guidewire.

It is the object of the present invention to provide an imaging guidewire that is not required to cross the lesion by itself. It crosses the lesion together with the catheter. This reduces the mechanical requirement of the guidewire. It also eases the physician's work and reduces blood vessel trauma or perforation.

It is another object of the present invention to provide an atherectomy device that cuts atheroma in a gentle manner, thus reducing restenosis.

Another object of the present invention is to provide an atherectomy device that cuts and remove in-stent restenosis in a gentle manner.

It is a further object of the present invention to provide an atherectomy device that cuts the atheroma safely, reducing the risk of artery perforation.

A still further object of the present invention is to provide an atherectomy device that gives the physician a real time artery cross-section image.

A still further object of the present invention is to provide an atherectomy device which includes balloons for radially positioning of the working head.

A still further object of the present invention is to provide an atherectomy device that allows the physician to control the longitudinal position and orientation of the working head.

A still further object of the present invention is to provide an atherectomy device that allows the physician to control the lumen's cross sectional area to be excised.

A still further object of the present invention is to provide an atherectomy device that enables opening of total occlusions.

A still further object of the present invention is to provide an atherectomy device that enables removal of atheroma at bifurcation.

A still further object of the present invention is to provide an atherectomy device which includes means for aspirating debris of the atheroma.

A still further object of the present invention is to provide an atherectomy device which includes lumen for supplying therapeutic liquid to the site of atheroma.

According to these and further objects of the present invention, which will become apparent as the description thereof is presented below; the present invention provides an atherectomy device which includes:

- A catheter assembly having a distal portion and adapted for insertion into a patient, said catheter assembly including an actuator and controller/computer unit;
- A piston located within the distal portion of the catheter assembly and adapted for simultaneous longitudinal and rotational movement therein, the first piston including an endless wave-shaped groove defined in a circumferential surface thereof;
- At least one ball retained for revolving motion in a recess defined in an interior surface of the distal portion of the catheter assembly, said ball projecting into and received by said groove to force said piston to rotate about its longitudinal axis in response to longitudinal movement of said piston;
- A working head secured to said piston for simultaneous longitudinal and rotational movement together with said piston;
- Positioning balloon located on the circumference of the catheter distal end;
- An imaging guidewire designed and constructed to position an operative portion of a catheter before a plaque (i.e. the guidewire does not traverse the plaque).

The imaging guidewire of this invention is unique in its mode of operation and its construction. In prior art the imaging guidewire that can produce a cross sectional image is required to cross the lesion. This requirement is problematic. Treating more calcified and/or longer lesions, pose higher risk of causing trauma to the blood vessel or perforation. ARIO's mode of operation does not require that the imaging guidewire will cross the lesion by itself. First, the physician inserts the imaging guidewire up to the lesion and then slides the catheter over the imaging guidewire up to the distal end of the imaging guidewire. Crossing the lesion is done by the catheter together with the imaging guidewire. The catheter advances slowly. The physician can see where he is heading and can control the radial position of the catheter with the positioning balloons, prior to operating the working head. This procedure eases the physician's work and minimizes blood vessel perforation.

In regard to the imaging guidewire technical requirements:

ARIO's imaging guidewire must withstand the following requirements:
1) Steerability—to allow the physician to direct the guidewire into the desired branch. A common solution is by manufacturing the guidewire with a bend at its distal end.
2) Flexibility—to allow easy advancement of the guidewire in curved blood vessel.
3) Torqueability—is needed because the distal tip of the guidewire is rotated from its proximal end.

However the fact that ARIO's mode of operation does not require that the imaging guidewire will cross the lesion by itself, markedly eases the pushability (axial force) and crossability (shape of the distal tip) requirements.

An additional technical advantage of the non-crossing the lesion imaging guidewire lies in the fact that the distal tip can be relatively large. This eases the incorporating of an imaging sensor in the distal tip. For example the distal tip of this invention can be 800 microns in diameter, while the rest of the guidewire is 350 microns in diameter. The larger the diameter of the sensor, the better is the image quality. Prior art teaches an imaging guidewire that has a small diameter along its entirety. U.S. Pat. No. 6,445,939 to Swanson describes an Optical Coherence Tomography (OCT) imaging guidewire, that is 350 microns (0.014") in diameter along its entirety which results in reduced image quality.

The present invention further provides a method of removing intraluminal occlusions which includes the following steps:
(a) Inserting an imaging guidewire into the blood vessel up to the occlusion, without crossing the lesion;
(b) Sliding the catheter over the imaging guidewire up to the distal end of the imaging guidewire;
(c) Securing proximal end of imaging guidewire to imaging guidewire motor;
(d) Connecting therapeutic infusion pump;
(e) Connecting debris vacuum pump;
(f) Operating balloon pumps and equally pressurizing the positioning balloons;
(g) Scanning the blood vessel with the imaging system to produce a cross section image of the blood vessel;
(h) Radially positioning the working head in a desired location by non-equally pressurizing the positioning balloons
(i) Operating the working head;
(j) Repeating steps (g) to (i) until the desired result is achieved;
(k) Deflating positioning balloons;
(l) Advancing the catheter distally; and
(m) Repeating steps (f) to (l) until the lesion is crossed.

Thus, according to one aspect of the present invention there is provided a method for reducing restriction of blood flow in a lumen of a blood vessel caused by an intraluminal plaque therein. The method includes: (a) inserting an imaging guidewire into the lumen of the blood vessel to the intraluminal plaque, the imaging guidewire capable of generating a cross-sectional image of the lumen; (b) propelling a catheter including a working head over the imaging guidewire towards the intraluminal plaque until the catheter reaches the distal end of the guidewire; (c) scanning the lumen with the imaging guidewire to generate the cross-sectional image of the lumen; (d) radially positioning the catheter in the lumen by actuating at least one positioning element; (e) monitoring the cross sectional image to ascertain that the working head is positioned at a desired location with respect to the proximal end of the intraluminal plaque; and (f) operating the working head to remove at least a portion of the intraluminal plaque.

According to another aspect of the present invention there is provided a system for reducing restriction of flow in a lumen of a blood vessel caused by an intraluminal plaque therein. The system includes:
(a) an imaging guidewire insertable in the lumen of the blood vessel, the imaging guidewire capable of generating digital data which describe a cross-sectional image of the lumen and communicating the digital data to a central processing unit (CPU) and further capable of guiding a catheter to the intraluminal plaque without traversing the plaque;
(b) the catheter including a working head, the working head designed and constructed to remove at least a portion of the intraluminal plaque;
(c) at least one positioning element integrally formed with, or attached to, the catheter, the at least one positioning element designed and constructed to radially position the working head within the lumen of the blood vessel, (d) the CPU and (e) the actuators, subject to control by the CPU and including: (i) at least one positioning element actuator responsible for the control of the at least one positioning device. The CPU is designed and configured to: (i) accept input from a physician; (ii) to receive the digital data which describe the cross-sectional image of the lumen and transform the digital data into the cross-sectional image displayable upon a display device; (iii) operate actuators which control components of the system; (iv) control operation of the positioning element by means of at least one of the actuators According to further features in preferred embodiments of the invention described below, the method further includes iteratively repeating (c) through (f) until the restriction of the lumen has been reduced to the desired degree.

According to still further features in the described preferred embodiments the method further includes repetition of (e) and (f).

According to still further features in the described preferred embodiments the method further includes iteratively repeated until the restriction of the blood flow in the lumen has been reduced to the desired degree.

According to still further features in the described preferred embodiments the method further includes advancing the catheter in the lumen.

According to still further features in the described preferred embodiments the method further includes iterative repetition of at least some of the actions until the working head traverses the intraluminal plaque.

According to still further features in the described preferred embodiments the intraluminal plaque is of a type selected from the group consisting of a primary atherosclerotic lesion, a lesion caused by restenosis, a lesion residing at least partially within a previously implanted stent, a lesion situated in close proximity to a bifurcation of the lumen of the blood vessel, a vulnerable plaque and a lesion which totally occludes the lumen of the blood vessel.

According to still further features in the described preferred embodiments the working head includes at least one cutting edge which is operative only when the working head moves rotationally.

According to still further features in the described preferred embodiments the at least one positioning element includes at least one balloon which circumferentially surrounds at least a portion of the catheter.

According to still further features in the described preferred embodiments the at least one positioning element includes at least one set of at least three balloons in a single cross sectional plane of the catheter.

According to still further features in the described preferred embodiments the method further includes at least one additional set of at least three balloons in a single cross sectional plane of the catheter.

According to still further features in the described preferred embodiments the inserting, propelling, scanning, radially positioning, monitoring and operating are subject to control by a single central processing unit (CPU).

According to still further features in the described preferred embodiments the single computerized control unit is further subject to input by a physician operator thereof.

According to still further features in the described preferred embodiments the operating the working head begins prior to a traversal of the plaque by the working head.

According to still further features in the described preferred embodiments the operating of the working head includes rotating the working bead at a speed of 1 to 100 RPM, more preferably at a speed of 5 to 50 RPM, most preferably at approximately 15 RPM.

According to still further features in the described preferred embodiments the CPU is further designed and configured to perform at least one action selected from the group consisting of: (i) to rotate the guidewire within the catheter by means of the actuators; and (ii) control operation of the working head.

According to still further features in the described preferred embodiments the CPU further includes at least one item selected from the group consisting of a display device and a data input device.

According to still further features in the described preferred embodiments the actuators further includes at least one additional actuator designed and constructed to perform at least one action selected from the group consisting of: (ii) rotate the working bead; (iii) advance the catheter within the lumen; and (iv) rotate the guidewire within the catheter. The actuators are subject to control of the CPU.

According to still further features in the described preferred embodiments the working head operates intermittently as the catheter traverses the intraluminal plaque. Traversal is preferably incremental.

According to still further features in the described preferred embodiments the working head includes at least one cutting edge which is operative only when the working head moves rotationally.

The present invention successfully addresses the shortcomings of the presently known configurations by providing minimally invasive surgical systems and methods of use thereof which permit traversal of a plaque via sequential removal of portions thereof, each of the portions selected from a cross sectional image made prior to the traversal.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Wherever possible, like reference numerals have been utilized to identify common elements throughout the figures.

In the drawings:

FIG. 1 is a longitudinal sectional view of the distal unit of ARIO according to one embodiment of the present invention.

FIG. 2 is a development into a plane view of the closed wave-shaped groove employed in the present invention.

FIG. 3 is a cross sectional view taken along lines 3-3 of FIG. 1.

FIG. 4b is a cross sectional view taken along lines 4b-4b of FIG. 4a.

FIG. 5 is a view in longitudinal section of one alternative embodiment of the distal end of the non-crossing the lesion imaging guidewire of the present invention.

FIG. 6 is a view in longitudinal section of an alternative embodiment of the working head of the present invention.

FIG. 12 is a side view of ARIO's actuator of the present invention.

FIG. 13 is a top view of ARIO's actuator of the present invention.

DETAILED DESCRIPTION OF THE PREFERRED EMBODIMENTS

Figure 4B:
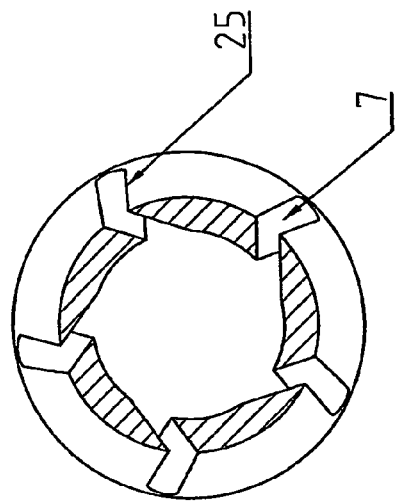

The present invention is of surgical systems and methods of use thereof which can be used to increase blood flow in a lumen of a blood vessel in a way which minimizes the risk of damage to surrounding portions of the vessel wall.

Specifically, the present invention can be used to provide improved computerized control for operation of atherectomy instruments which results in improved methods for intravascular surgery.

The principles and operation of methods and systems according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

ARIO combines two main operational features. First, ARIO is able to rotate a working head at a very low speed of rotation (less than 100 RPM) and at high cutting moment. This is in contrast to previously known devices such as AtheroCath™ and the Rotablator™ that rotate at speeds of 190,000, and 2,000 RPM respectively. Second, ARIO's working head is not forced through the lesion prior to operation, but is rather slowly advanced by small increments while cutting the plaque. This prevents stretching the vessel and resultant damage. As a result of these features, minimal trauma to the artery is incurred. This is of utmost importance as medical research has shown that the rate of restenosis is proportional to the trauma caused to the vessel during the angioplasty procedure.

Thus, the present invention includes several improvements and additions with respect to my own U.S. Pat. No. 5,350,590. The main improvements and additions are:

1) Incorporation of a non-crossing the lesion imaging guidewire.
2) Incorporation of positioning balloons.
3) Replacing of the hydraulic power by a pushable shaft in the manner described in my U.S. Pat. No. 5,806,404, FIG. 5.
4) Alternative working head that has a cone shape,
5) The pins that protrude in the closed wave-shaped groove are replaced by balls.
6) Alternative construction of the closed wave-shaped groove.

For purposes of this specification and the accompanying claims, the phrase "working head" should be construed in its broadest possible sense. Thus a working head may include, but is not limited to, a rotary cutting nose cone, an abrasive nose cone, a laser energy delivering device, an ultrasound energy delivering device, a heat delivering device, a blunt dissection device or a blunt abrasive device. The structural interrelations between the working head and the catheter may vary depending on the nature of the working head, so long as effective guidance of the working head to establish a path across the occlusion during its intermittent operation is achievable.

It is expected that during the life of this patent many relevant minimally invasive medical imaging techniques that can generate a cross-sectional view of the blood vessel will be developed and the scope of the terms "image" and "imaging" is intended to include all such new technologies a priori.

The ARIO device comprises three main units: The distal unit, the proximal unit, and two tubes that connect the distal and the proximal units. ARIO is operated by an actuator that is controlled by a controller/computer unit (CPU). There are two additional components that are needed for ARIO's operation: The first is a vacuum pump for removing atheroma debris and blood clots and the second is a therapeutic liquid infusion pump. These components are commercially available and one of ordinary skill in the art will readily be able to incorporate the commercially available pumps into the context of the present invention.

Referring now to the drawings, FIG. 1 illustrates a longitudinal sectional view of the distal unit of ARIO. It is shown a blood vessel (21) that has atheroma (22). A pushable shaft (1) moves back and forth, forcing the piston (2) to reciprocate longitudinally in a cylinder (12). Balls (3) located in a closed wave-shaped groove (4) are held in place by holder (10), and force piston (2) to rotate. The connection of the pushable shaft (1) to the piston (2) is via a bearing adapter (11) and spherical plain bearing (5). Spherical plain bearing (5) decouples the pushable shaft (1) from the rotation movement of the piston (2), i.e., the pushable shaft (1) is not rotating during the operation. A working head (6) is fixedly attached to the piston (2) thus performing a combined longitudinal and unidirectional rotational motion. The pushable shaft (1) is a flexible tube with enough axial stiffness to push and pull piston (2). Pushable shaft (1) is located within torque tube (13). Flexible tube (13) has enough torsion stiffness to counter the moment created by the working head (6). The outside diameter of pushable shaft (1) is PTFE coated in order to decrease friction between it and torque tube (13).

The working head (6) contains several sharp edge openings (7) through which the excised atheroma is forced into the cavity (8). The debris is then removed from the blood vessel by suction of a vacuum pump via the plenum (9). Torque tube (13) is connected to cylinder (12). Three positioning balloons (14) are mounted on the outer circumference of torque tube (13). Lumens (15) in the circumference of the torque tube (13) enable inflating/deflating the three positioning balloons (14). The role of the positioning balloons will be explained in details in FIG. 3 and FIG. 7 to FIG. 9.

ARIO accommodates a non-crossing the lesion imaging guidewire (16). Like a standard guidewire it has a body in the form of an elongated flexible tubular member. The imaging guidewire (16) has a proximal end and a distal end. Although imaging guidewire (16) is shown in the drawings to be straight along the catheter, when the imaging guidewire is outside the catheter its distal end resembles a standard guide wire (i.e., its distal tip is bent to allow for steerability).

The preferred imaging method used in this embodiment is Optical Coherence Tomography (OCT). OCT uses infra red light waves that reflect back from the vessel wall to produce a real time computer processed images cross section. OCT in conjunction with appropriate software can produce a 3 dimensional image of the blood vessel. The resolution of the images can reach 10 microns.

The distal end of imaging guidewire (16) comprises a folding mirror (17) that is optically coupled to a grin lens (18), and a preformed curved tip transparent to light energy (20) that encapsulates the folding mirror (17). In some embodiments of the invention the folding mirror (17) and the grin lens (18) protrude in front of the working head. In the preferred embodiment, shown in FIG. 1, only folding mirror (17) protrudes in front of the working head. This design minimizes the trauma to the blood vessel. It is an important feature of the present invention that the angle between folding mirror (17) and the catheter axis may vary, thus enabling the image to be taken at cross sections distally or proximally to the folding mirror (17). In the arrangement shown in FIG. 1 the angle is 45 degrees and therefore the image is taken at the section of the folding mirror (17). An optical fiber (19) is optically coupled to the grin lens (18). The optical fiber (19) extends, via a central lumen, all over the imaging guidewire (16) up to the proximal end where it is coupled to an optical connector (not shown in drawing). For understanding the function of these elements the reader is referred to U.S. Pat. No. 6,445,939 to Swanson.

In order to get an image of the circumference of the blood vessel wall (21) the imaging guidewire (16) is rotated. The number of revolutions of the imaging guidewire (16) is dictated by technical requirements e.g., whether video or still images are required. It is preferable that surface (27) of the working head (6), where the imaging guidewire (16) slides, will be Teflon coated. It is to be noted that while the image is taken, the catheter is held in place by the positioning balloons (14). This fact results in a better image.

It is clear that in order to accurately radially position the catheter in the lumen by inflating/deflating the balloons (14) the physician must know the relative orientation between the folding mirror (17) and the balloons. This can be done either mechanically or by software. For mechanical orientation the proximal end of the imaging guidewire has a mechanical key (66), shown in FIG. 15. The mechanical key (66) can be of various designs e.g., it may have a "D" shape. Whatever the shape of "key" 66, its function is to assure that when the imaging guidewire is located inside the catheter there is a fixed orientation between the folding mirror and the balloons.

Alternatively, orientation may be accomplished by software. In this case the orientation of the folding mirror (17) in regard to balloons (14) is arbitrary. The balloons are inflated sequentially. Following each inflation, a cross sectional image of the lumen is taken. By comparing the images the orientation of the folding mirror to the balloons can be calculated.

The rotation of the imaging guidewire inside the catheter can be exploited to facilitate the movement of the atheroma debris towards the proximal end. This is in addition to the vacuum force exerted on the debris. This goal may be achieved, for example, by incorporating an Archimedes screw into the design of the imaging guidewire. Archimedes screw (67) is shown in FIG. 1 and also in FIG. 15. Archimedes screw may extend along the imaging guidewire or only at a small part of the imaging guidewire. In FIG. 1 it is shown a screw that extends from working head (6) to the bearing adapter (11). Screw (67) expedites movement of plaque debris removed by working head (6) in plenum (9) that is narrow.

Alternatively the imaging method can be any of the minimally invasive modalities mentioned above e.g., Ultrasound. Ultrasound produces images from back-scattered sounds of the vessel wall. The general outer shape of the imaging guidewire will be the same as for OCT, while the inner parts will be different. For understanding the operation of an ultrasound imaging guidewire the reader is referred to U.S. Pat. No. 5,095,911 to Pomeranz. It is important to stress that the requirement that the imaging guidewire rotates along its axis is not mandatory. Imaging guidewires that can produce an image without rotation are known, e.g., U.S. Pat. No. 5,947,905 to Hadjicostis which describes an ultrasound transducer where the signals are received from an array of sensors located all around the circumference of the imaging guidewire.

FIG. 2 is a development into a plane view of the closed wave shaped groove (4). The closed wave shaped groove (4) comprises three types of sections. A positive slopped section (4a), a negative sloped section (4b) and a parallel to catheter axis section (4c). The end points of the positive sloped section (4a) are located distally to the end points of the negative sloped section (4b), at a distance that is the length of the parallel to catheter axis section (4c). The parallel to axis section (4c) is connecting the end points of the two sloped sections (4a and 4b). It is the aim of the following discussion to show that the closed wave shaped groove (4) transforms a reciprocating motion of piston (2) into a combined reciprocating and uni-directional motion of piston (2). Lets start with an arbitrary position of ball (3) in the closed wave shaped groove (4). It is important to understand that the ball (3) is fixed in the catheter while closed wave shaped groove (4) slides over it. When distal piston (2) is pulled proximally it also performs a clock-wise rotation when viewed from proximal end. This motion continuous until end point (4a-1) reaches the center of the ball (3). Then if the longitudinal motion of piston (2) is changed i.e, it is pushed distally, end point (4b-1) will reach the center of ball (3). This part does not result in rotation of piston (2). However, if piston (2) continues to be pushed distally the negative sloped section (4b) will slide over ball (3) causing piston (2) also to perform a clockwise rotation when viewed from proximal end. This motion will continue until end point (4b-2) reaches the center of ball (3). The above discussion can be repeated for other apexes of the closed wave shaped groove (4). Thus, it was shown that the closed wave shaped groove (4) transforms a reciprocating motion of piston (2) into a combined reciprocating and uni-directional rotational motion of piston (3).

In order to cause piston (2) to rotate in the opposite direction, (i.e. counter-clock-wise rotation, when viewed from proximal end), the end points of the positive slopped section (4a) must be located proximally to the end points of the negative sloped section (4b), at a distance that is the length of the parallel to catheter axis section (4c).

The stroke of the closed wave-shaped groove can vary. For example, in the device shown in FIG. 1, which is a scaled drawing of ARIO 2.3 mm(=7 F) the stroke is 2 mm.

FIG. 3 shows the operation of the positioning balloons (14). The position of the catheter is a resultant of the forces applied by the three positioning balloons (14) on the lumen's wall. If the balloons are inflated by unequal pressures the catheter will move off axis. In the drawing positioning balloon (14a) is inflated more then positioning balloons (14b) and (14c). Therefore, the catheter will move downwards. Positioning balloons (14 a-c) can be replaced by other positioning elements such as mechanical arms that are located on the outer circumference of the catheter and are pushed during deployment against the lumen's wall. Also, are shown the lumens (15) one for each of the positioning balloons (14). An additional therapeutic lumen (26) is used for injection of therapeutic liquid to the area of the excised atheroma. The therapeutic lumen may also serve additional purposes. For example, it has been observed that there is a substantial attenuation in the imaging signal resulting from the presence of blood. In order to overcome this problem injection of saline at the place of imaging is required. The therapeutic lumen can serve this purpose. Alternatively, the saline can be injected via an additional lumen or via the imaging guidewire itself.

It is to be noted that the three positioning balloons (14) are connected to a control system (located outside the patient's body) that measures and regulates the pressure in each of the positioning balloons (14). The control system assures that the pressure in any of the positioning balloons (14) will not rise above a predetermined threshold pressure (e.g., 4 atmospheres). This is an important feature as it eliminates stressing of the vessel walls. Balloons can be manufactured from different materials (PET, latex, silicon etc.). It is preferred to use low pressure elastomeric balloons, typically made of latex or silicone that stretch 100-600% when pressure is applied, and return to their original size when pressure is released.

Figure 7:
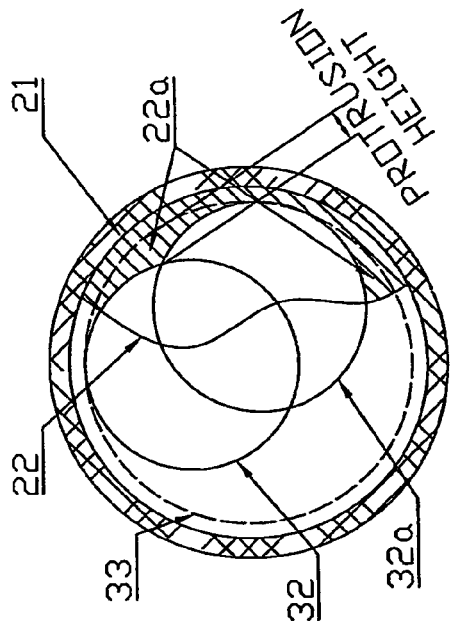
FIG. 7 is a diagrammatic illustration showing the way In-Stent restenosis is removed from inside the stent according to the present invention.
Figure 8:
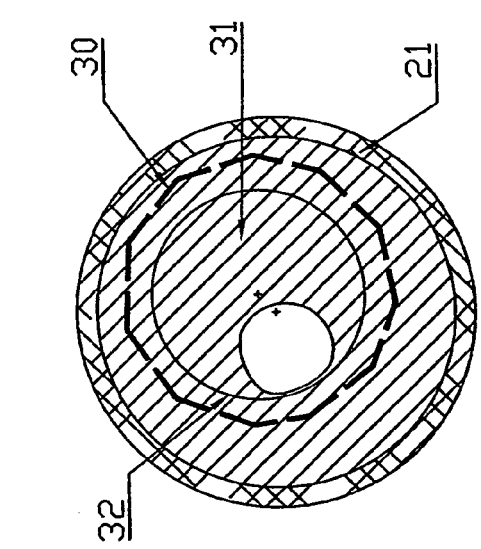
FIG. 8 is a diagrammatic illustration showing the way plaque is removed from a blood vessel that has a diameter substantially greater then ARIO's diameter, according to the present invention.
Figure 9:
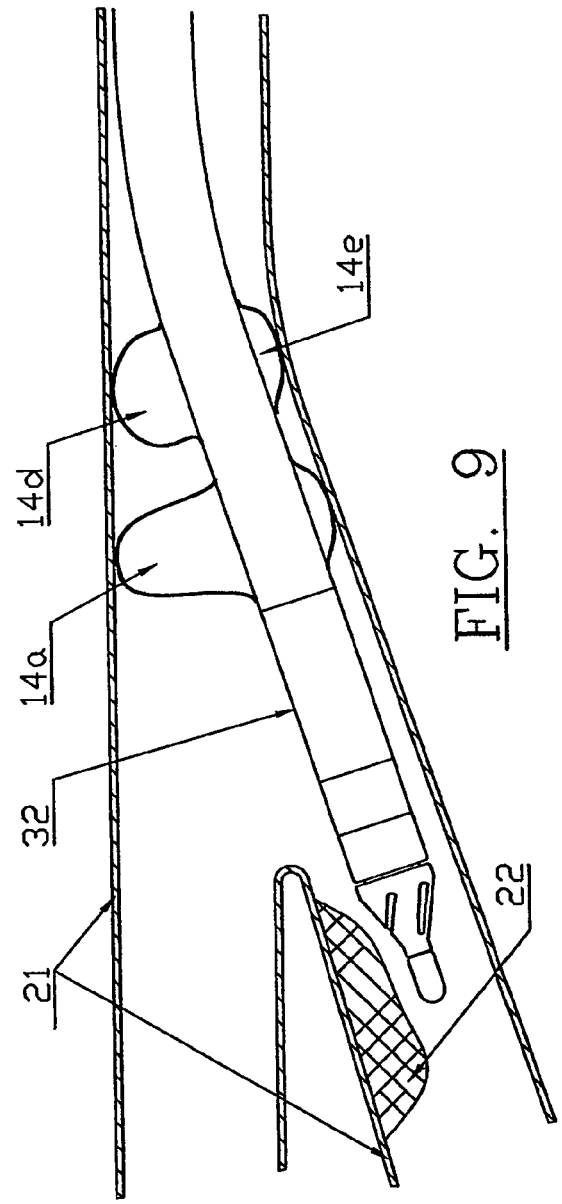
FIG. 9 is a diagrammatic illustration showing the way plaque located at bifurcation is removed, according to the present invention.

An additional embodiment comprises a single positioning balloon 14. In this case the catheter will always be positioned on the longitudinal axis of the lumen. However, this embodiment limits the operation of ARIO. A disadvantage of using one positioning balloon is that blood cannot flow in the artery when the balloon is inflated, thus causing pain to the patient. In the case of three or more balloons, blood can always flow via the gaps between the balloons. FIGS. 7 to 9 show the operational advantages of using multiple positioning balloons (14).

Figure 4C:
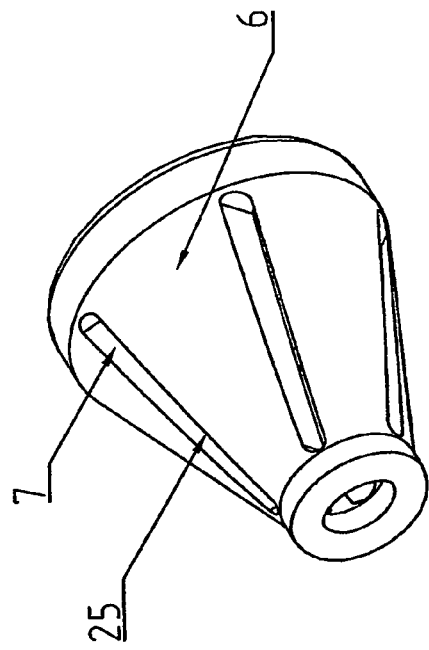
FIG. 4c is an isometric view of the working head of the present invention.
Figure 4A:
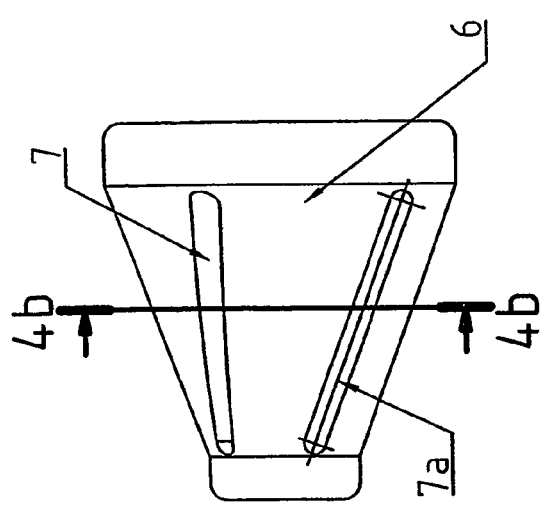
FIG. 4a is a planar view of the working head of the present invention

FIGS. 4a, 4b and 4c show the cone shaped working head (6). It can have one or more openings (7) with sharp edges (25). The pictured embodiment shows five openings (7). It is the goal of this design to have a cutter that is safely inserted in the blood vessel in spite of having very sharp edges. Openings (7) are very narrow, so that debris of the excised atheroma that enters cavity (8; see FIG. 1) cannot go outside of working head (6) into the blood vessel. The opening (7) is manufactured with a cutter (e.g., laser cutter). Sharp edges (25) are created if the cutter is positioned so that it cuts perpendicular to a plane passing through the cutter (6) axis and the cutting pass (7a) is parallel to the contour line of the cone. When looking on the working head (6) axially towards the proximal direction, the sharp edges (25) are not seen. This means that if the working head (6) comes in contact with the vessel's wall, the wall touches a smooth surface, rather than the sharp edges. This permits safe insertion of the device into the blood vessel. The cutting of the atheroma is possible only when working head (6) rotates.

FIG. 5 shows an imaging guidewire (16) that has the same diameter (e.g., 350 microns) along its entire length. This small diameter guidewire includes a small diameter lens (18), as described in U.S. Pat. No. 6,445,939 to Swanson. This construction allows only a small part of the imaging guidewire (16) to protrude in front of working head (6). This minimizes the trauma to the blood vessel. The part that protrudes includes folding mirror (17) that is located in preformed curved tip transparent to light energy (20). Also are shown lens (18) and optical fiber (19). Imaging guidewire (16) rotates on a sliding surface (27). A ring (28) is fixed to distal end of imaging guidewire (16), thus preventing imaging guidewire (16) from being pulled back beyond sliding surface (27).

FIG. 6 shows an alternative embodiment of the working head (6). The working head (6) has opening (7) on its distal surface. The distal end of imaging guidewire (16) is substantially bigger then its other parts. In order to reduce the part of the imaging guidewire (16) that extends in front of working head (6) a recess (29) is done in the front face of working head (6). This construction minimizes the trauma to the blood vessel. The part that protrudes out of working head (6) front face includes only folding mirror (17) that is located in preformed curved tip transparent to light energy (20). Imaging guidewire (16) rotates on a sliding surface (27). Also are shown lens (18) and optical fiber (19). This embodiment has advantages when used for clearing total occlusions (22).

FIG. 7 shows the struts of a stent (30) that is deployed off blood vessel axis. This phenomenon can happen either during the deployment of the stent or subsequently. In order to excise the in-stent Restenosis (31), without damaging the stent (30), the catheter (32) must be positioned on the stent axis rather then on the blood vessel axis. The radial positioning is achieved by positioning balloons (14).

FIG. 8 shows a catheter (32) that has a diameter that is significantly smaller than the diameter of the blood vessel. In minimally invasive procedures it is preferred to use a small diameter catheter (e.g., no more then 2.3 mm=7 F), so that only a small incision in the groin is needed to introduce the catheter (32). Nonetheless, this small diameter catheter (32) must remove the atheroma that may completely traverse the cross section of the blood vessel (21). The positioning balloons enable the physician to move the catheter radially all over the cross section of the blood vessel. The physician can define an imaginary border line (33) in which he wants the atheroma to be removed. The border line (33) diameter is smaller then the inside diameter of the blood vessel (21), thus reducing the risk of blood vessel perforation. It is clear, from geometric considerations, that initial atheroma (22) can never be totally removed in this procedure. Two sequential positions of the catheter (32) and (32a) are shown in the drawing. Some protrusion of atheroma (22a) will always be left. The protrusion (22a) can be defined by its height, as shown in the drawing. In order to make the protrusion height smaller, and thus making the inner surface of blood vessel (21) smoother, more sequential catheter positioning with closer distances between their centers must be done. The sequential radial positioning of the catheter can be done either manually or automatically.

FIG. 9 shows how positioning balloons 14 are used to remove atheroma (22) at bifurcation. In this case the positioning balloons are used to position the catheter (32) not only off axis but also at an angle to the axis of the blood vessel (21). This can be done if an additional array of 3 positioning balloons (14d, 14e, 14f) (14f is not shown in drawing) is added along the catheter (32). If positioning balloon (14a) is inflated more than positioning balloon (14d), catheter (32) will be forced to move towards the atheroma (22).

Although my U.S. Pat. No. 5,697,459 shows a similar arrangement of 6 balloons, their main purpose is to enable the drill to be self propelled. Therefore, that earlier work depicts 3 balloons located on the device body and 3 other balloons located on the working head. According to the present invention (ARIO) all the positioning balloons are all located on the catheter body.

Figures 10, 11:
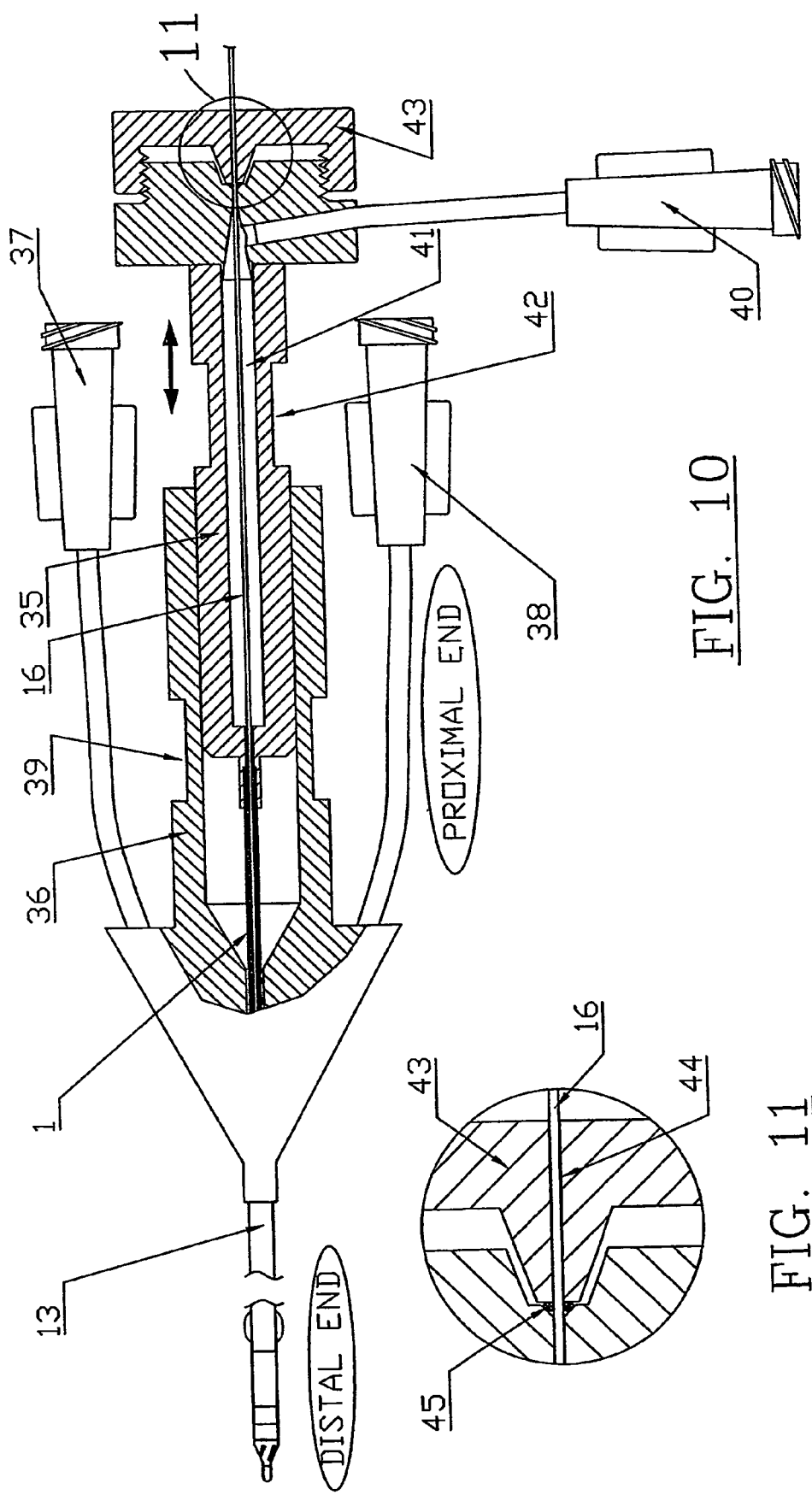
FIG. 10 is view in longitudinal partial section of the proximal end of ARIO of the present invention.
FIG. 11 is a detailed view in longitudinal section of the O-ring region shown in FIG. 10.

FIG. 10 shows the proximal end of ARIO. The distal end of ARIO is shown for reference only. It shows a proximal piston (35) that moves back and forth in a proximal cylinder (36). The stroke of this movement corresponds to stroke of the closed wave-shaped groove (4) shown in FIGS. 1 and 2. The velocity of proximal piston (35) can be very low. In the preferred embodiment it is 1 mm/sec. This velocity is transformed at the distal end of ARIO to 15 RPM of the working head (6).

Proximal cylinder (36) is fixedly attached to torque tube (13). An infusion connector (37) is mounted on proximal cylinder (36). Infusion connector (37) is opened to therapeutic lumen (26; see FIG. 3). An infusion pump is connected to the infusion connector (37) to deliver therapeutic liquid, via therapeutic lumen (26; see FIG. 3), to the site of the atheroma. Infusion pumps suited for use in the context of the present invention are commercially available. One of ordinary skill in the art will be easily able to incorporate such a commercially available device into the present invention. Three balloon connectors (38) (for clarity only one is shown) are connected to proximal cylinder (36). Balloon connectors (38) are opened to balloon lumen (15; see FIG. 3). Proximal cylinder (36) includes a groove (39) on its circumference. Groove (39) is used to mount proximal cylinder (36) on ARIO actuator (It is explained in FIG. 12 and FIG. 13).

Proximal piston (35) is fixedly attached to pushable shaft (1). A vacuum connector (40) is mounted on proximal piston (35). Vacuum connector (40) is opened to passage (41), that is connected to plenum (9) shown in FIG. 1. A vacuum pump (not shown here) is connected to vacuum connector (40) for aspirating the atheroma debris via passage (41) and plenum (9) (see FIG. 1). Proximal piston (35) includes a groove (42) on its circumference. Groove (42) is used to mount proximal piston (35) on ARIO actuator. (It is explained in FIG. 12 and FIG. 13). An imaging guidewire nut (43) is attached to the proximal end of proximal piston (35).

FIG. 11 is an enlargement of detail 11 shown in FIG. 10. Imaging guidewire nut (43) has a central passage (44) through which imaging guidewire (16) passes. When imaging guidewire nut (43) is tightened it squeezes on an O-ring (45) thus keeping the proximal piston passage (41) vacuum tight. O-ring (45) allows imaging guidewire (16) to rotate, while keeping the vacuum tight. The rotation of imaging guidewire (16) is needed for the imaging process.

FIGS. 12 and 13 describe ARIO's actuator. FIG. 12 is a side view of the actuator and FIG. 13 is a top view of the actuator. A base (48) is fixed to the patient bed. A linear slide (49) is attached to an advancement linear actuator (50). Both are mounted on base (48). They serve for advancing ARIO in the blood vessel. The advancement is incremental with a movement that is preferably less then the stroke of the closed wave-shaped groove (4) (see FIG. 2). A bracket (51) is mounted on top of linear slide (49). Groove (39) of proximal cylinder (36) (see FIG. 10) fits into bracket (51) and secured in place by clamp (52). Linear slide (54) is attached to a reciprocating linear actuator (55). Both are mounted on bracket (51). An adapter (60) is mounted on top of linear slide (54). Groove (42) of proximal piston (35) (see FIG. 10) fits into adapter (60) and secured in place by clamp (53). Back and forth motion of reciprocating linear actuator (55) causes reciprocation of proximal piston (35) and pushable shaft (1) and eventually results in longitudinal and rotational movement of working head (6) (see FIG. 1).

FIG. 13 also depicts a balloon inflating/deflating system. It comprises a syringe pump (56) that is connected to balloon connector (38) (see FIG. 10). Syringe pump (56) is operated by balloon linear actuator (58). A pressure transducer (57) measures the pressure in syringe pump (56). This pressure is monitored by a controller/computer unit (see FIG. 14 and explanation hereinbelow). For clarity, only one balloon inflating/deflating system is shown, but the actual system may, for example, contain three or six balloons which are independently regulated.

ARIO's actuator comprises also an imaging guidewire motor (59). The imaging guidewire (16) is secured to motor (59). In order to take a circumferential scan of the artery the imaging guidewire must rotate. This is done by imaging guidewire motor (59). The signals of the scanning are sent to the computer via optical fiber (19).

Figure 14:
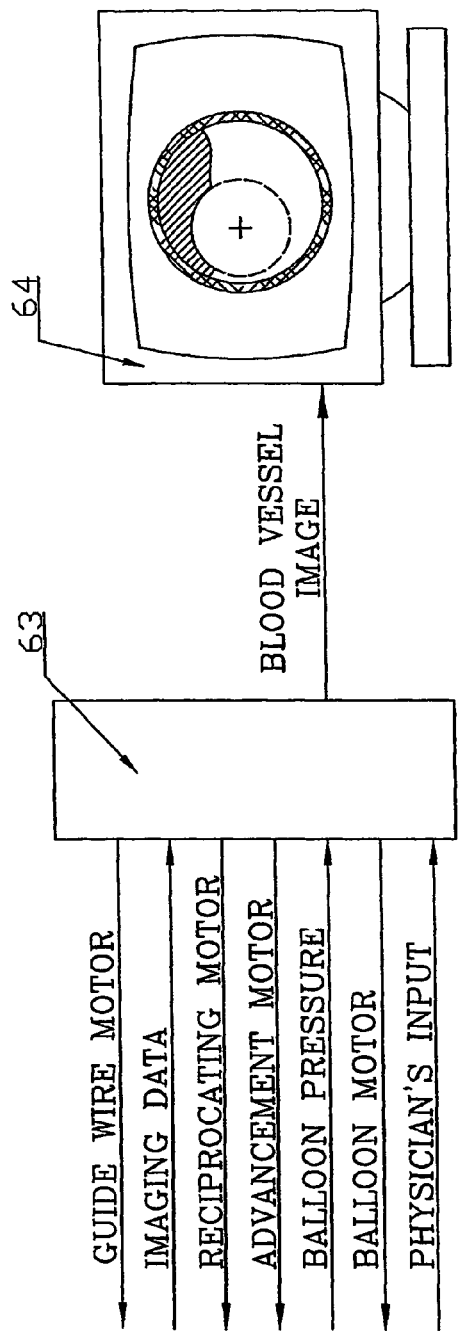
FIG. 14 is a schematic drawing of the ARIO's controller/computer unit of the present invention.

FIG. 14 is a schematic drawing of ARIO's control system. It comprises a controller/computer unit (63) and a display (64). The controller/computer unit (63) governs all the functions of the system. The inputs to the controller/computer unit are: a) balloon pressure b) imaging data c) physician inputs: advancement velocity, reciprocation velocity, maximum balloon pressure, balloon positioning, cutting border line (33) (see FIG. 8). The outputs from the controller/computer unit (63) are directed to: a) advancement linear actuator (50); b) reciprocating linear actuator (55); c) imaging guidewire motor (59); d) balloon linear actuator (58) and e) processed optical image of the blood vessel to the display. The controller/computer unit (63) controls the movement of balloon linear actuator (58) in such a way that while one of the positioning balloons (14) moves in a desired direction, the pressure in the other positioning balloons does not exceed a predetermined threshold pressure (e.g., 4 Atmospheres). During the operation the physician sees a real time cross sectional images of the blood vessel. It is clear that the computer can construct a 3 dimensional image from the cross sections. The physician can see the atheroma in 3 dimensional image before and after operation. He can find out how much volume of atheroma was removed, calculate the surface roughness after the operation etc.

The operation of ARIO can be done automatically from the step that ARIO is positioned proximally to the lesion. However, the physician can always take control of the operation. Physician control may be either by direct physical manipulation of components of the system, or via input to the CPU.

The system further includes safety provisions, e.g., the electrical current of the advancement linear actuator (50) is limited so that no excessive force is applied on the blood vessel during advancement. The same applies to reciprocating linear actuator (55), so that the moment applied by working head is limited etc. The physician will be notified visually and/or audibly of any problem in the system.

Figure 15:
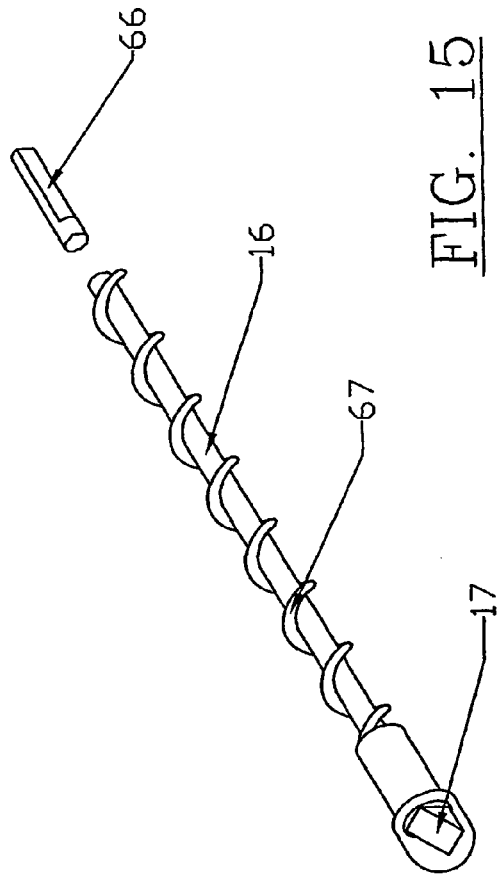
FIG. 15 is an isometric view of an imaging guidewire according to one embodiment of the present invention.

FIG. 15 illustrates clearly an imaging guidewire (16) with a mechanical key (66) and Archimedes screw (67). These features are illustrated within catheter (32) in FIG. 1, described hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for reducing restriction of blood flow in a lumen of a blood vessel caused by an intraluminal plaque therein, the method comprising:
    (a) inserting an imaging guidewire into the lumen of the blood vessel up to the intraluminal plaque without traversing the plaque, said imaging guidewire having a distal tip that includes imaging components capable of generating a cross-sectional image of the lumen, at least a portion of said distal tip having a diameter that is larger than a rest of said guidewire having a smaller diameter;
    (b) propelling a catheter over said imaging guidewire towards said intraluminal plaque until said catheter reaches said distal end of said guidewire, said catheter having a working head located at a distal tip of said catheter, said working head configured for removal of at least a portion of the intraluminal plaque, said catheter and said working head deployed on said imaging guidewire so as to accept passage of said rest of said imaging guidewire having said smaller diameter axially through a central region of said working head and said catheter as said catheter propelled towards said intraluminal plaque, and when said catheter reaches said distal tip of said guidewire at least a portion of said imaging components are positioned inside said working head and a portion of said distal tip the only element of either of said imaging guidewire and said catheter extending in front of said working head;
    (c) scanning the lumen with said imaging guidewire to generate said cross-sectional image of the lumen;
    (d) positioning said catheter in the lumen by actuating at least one positioning element;
    (e) monitoring said cross sectional image to ascertain that said working head is positioned at a desired location with respect to said proximal end of the intraluminal plaque; and
    (f) operating said working head to remove at least a portion of the intraluminal plaque.

2. The method of claim 1, further comprising repetition of (c) through (f).

3. The method of claim 2, iteratively repeated until the restriction in the lumen has been reduced to a desired degree.

4. The method of claim 3, further comprising advancing the catheter together with said distal tip of said guidewire in the lumen.

5. The method of claim 4, iteratively repeated until said working head traverses said intraluminal plaque.

6. The method of claim 1, wherein said intraluminal plaque is of a type selected from the group consisting of a primary atherosclerotic lesion, a lesion caused by restenosis, a lesion residing at least partially within a previously implanted stent, a lesion situated in close proximity to a bifurcation of the lumen of the blood vessel, a vulnerable plaque and a lesion which totally occludes the lumen of the blood vessel.

7. The method of claim 1, wherein said working head includes at least one cutting edge which is operative only when said working head moves rotationally.

8. The method of claim 1, wherein said positioning of said catheter in the lumen is implemented such that said at least one positioning element includes at least one balloon which circumferentially surrounds at least a portion of said catheter.

9. The method of claim 1, wherein said positioning of said catheter in the lumen is implemented such that said at least one positioning element includes at least one set of at least three balloons in a single cross sectional plane of said catheter.

10. The method of claim 9, wherein said positioning of said catheter in the lumen is implemented so as to further include at least one additional set of at least three balloons in a single cross sectional plane of said catheter.

11. The method of claim 1, wherein said inserting, propelling, scanning, positioning, monitoring, operating are subject to control by a single central processing unit (CPU).

12. The method of claim 11, wherein said single CPU is further subject to input by a physician operator thereof.

13. The method of claim 1, wherein said operating said working head begins prior to a traverse of the plaque by said working head.

14. The method of claim 1, wherein said operating of said working head includes rotating said working head at a speed of 1 to 100 RPM.

15. The method of claim 1, wherein said operating of said working head includes rotating said working head at a speed of 5 to 50 RPM.

16. A system for reducing restriction of flow in a lumen of a blood vessel caused by an intraluminal plaque therein, the system comprising:
  a) an imaging guidewire insertable in the lumen of the blood vessel up to the intraluminal plaque without traversing the plaque, said imaging guidewire having a distal tip that includes imaging components capable of generating digital data which describe a cross-sectional image of the lumen and communicating said digital data to a central processing unit (CPU) and further capable of guiding a catheter to the intraluminal plaque without traversing the plaque, at least a portion of said distal tip having a diameter that is larger than a rest of said guidewire having a smaller diameter;
  (b) a catheter including a working head located at a distal tip of said catheter, said working head designed and constructed to remove at least a portion of the intraluminal plaque, said working head deployed on said imaging guidewire so as to accept passage of said rest of said imaging guidewire having said smaller diameter axially through a central region of said working head and said catheter as said catheter is propelled towards said intraluminal plaque until said catheter reaches a distal tip of said guidewire such that at least a portion of said imaging components are positioned inside said working head and a portion of said distal tip is the only element of either of said imaging guidewire and said catheter extending in front of said working head;
  (c) at least one positioning element integrally formed with, or attached to, said catheter, said at least one positioning element designed and constructed to position said working head within the lumen of the blood vessel;
  (d) a CPU designed and configured to:
    (i) accept input from a physician;
    (ii) to receive said digital data which describe said cross-sectional image of the lumen and transform said digital data into said cross-sectional image displayable upon a display device;
    (iii) operate actuators which control components of the system; and
    (iv) control operation of said positioning element by means of at least one of said actuators; and
  (e) one or more actuators, subject to control by said CPU and including:
    (i) at least one positioning element actuator responsible for the control of said at least one positioning device.

17. The system of claim 16, wherein said CPU is further designed and configured to perform at least one action selected from the group consisting of:
  (i) to rotate said guidewire within said catheter by means of said actuators; and
  (ii) control operation of said working head.

18. The system of claim 16, wherein said CPU further includes at least one item selected from the group consisting of a display device and a data input device.

19. The system of claim 16, wherein said actuators further includes at least one additional actuator designed and constructed to perform at least one action selected from the group consisting of:
  (i) longitudinally reciprocate and rotate said working head;
  (ii) advance said catheter within the lumen;
  (iii) rotate said guidewire within said catheter; wherein said actuators are subject to control of said CPU.

20. The system of claim 16, wherein said working head is configured to operate intermittently as said catheter traverses said intraluminal plaque.

21. The system of claim 16, wherein said working head includes at least one cutting edge which is operative only when said working head moves rotationally.

22. The system of claim 16, wherein said at least one positioning element includes at least one balloon which circumferentially surrounds at least a portion of said catheter.

23. The system of claim 16, wherein said at least one positioning element includes at least one set of at least three balloons in a single cross sectional plane of said catheter.

24. The system of claim 23, further including at least one additional set of at least three balloons in a single cross sectional plane of said catheter.

25. The system of claim 16, wherein said working head is configured such that operation of said working head begins prior to a traverse of the plaque by said working head.

26. The system of claim 16, wherein operation of said working head includes rotating said working head at a speed of 1 to 100 RPM.

27. The system of claim 16, wherein operation of said working head includes rotating said working head at a speed of 5 to 50 RPM.

28. The system of claim 16, wherein said imaging guidewire further includes a imaging sensor and wherein said catheter is positionable upon said guidewire so that only said imaging sensor protrudes from said working head in a direction facing the plaque.

29. The system of claim 16, wherein an Archimedes screw is further incorporated into the design of said imaging guidewire in order to facilitate removal of at least a portion of the plaque.

30. The system of claim 16, wherein said catheter includes at least one therapeutic lumen.

31. The system of claim 16, wherein said catheter includes a central vacuum lumen.

32. The system of claim 16, wherein said catheter and said guidewire are configured to cross the lesion together by advancing said catheter together with said distal tip of said guidewire in the lumen.

33. A system for reducing restriction of flow in a lumen of a blood vessel caused by an intraluminal plaque therein, the system comprising:
  (a) an imaging guidewire insertable in the lumen of the blood vessel, said imaging guidewire has a distal tip that includes at least an imaging sensor and at least a portion of said distal tip has a diameter that is larger than a rest of said guidewire having a smaller diameter, said imaging guidewire capable of generating digital data which describe a cross-sectional image of the lumen and communicating said digital data to a central processing unit (CPU) and further capable of guiding a catheter to the intraluminal plaque without traversing the plaque;
  (b) said catheter includes a working head, said working head deployed on said imaging guidewire so as to accept passage of said rest of said imaging guidewire having said smaller diameter axially through a central region of said working head and said catheter as said catheter is propelled over said imaging guidewire until said working head reaches said distal tip, said working head designed and constructed to remove at least a portion of the intraluminal plaque; and (c) at least one positioning element integrally formed with, or attached to, said catheter, said at least one positioning element designed and constructed to radially position said working head within the lumen of the blood vessel.

34. The system of claim 16, wherein said at least a portion of said distal tip that is larger than the rest of the guidewire is a preformed curved tip.

35. The system of claim 16, wherein said at least a portion of said distal tip that is larger than the rest of the guidewire is a ring that is fixed to distal end of imaging guidewire.

36. The system of claim 16, wherein said at least a portion of said distal tip has a diameter of up to 800 microns, while the rest of the guidewire has a diameter of up to 350 microns.

* * * * *